(12) United States Patent
Andersson

(10) Patent No.: US 7,160,925 B2
(45) Date of Patent: Jan. 9, 2007

(54) DECOMPOSING SURFACTANT

(75) Inventor: Martin Andersson, Stockholm (SE)

(73) Assignee: Yki, Ytkemiska Institutet AB, Stockholm (SE)

( * ) Notice: Subject to any disclaimer, the term of this patent is extended or adjusted under 35 U.S.C. 154(b) by 437 days.

(21) Appl. No.: 10/837,617

(22) Filed: May 4, 2004

(65) Prior Publication Data

US 2005/0250861 A1   Nov. 10, 2005

(51) Int. Cl.
*B01D 17/05*   (2006.01)
*C07C 69/66*   (2006.01)
*C07C 69/72*   (2006.01)
*C07C 59/185*   (2006.01)

(52) U.S. Cl. ............... 516/157; 560/174; 560/178; 562/577

(58) Field of Classification Search ............... 516/157
See application file for complete search history.

(56) References Cited

U.S. PATENT DOCUMENTS 4,561,913 A    12/1985  Zado
5,789,371 A *   8/1998  Tracy et al. ............... 510/490

FOREIGN PATENT DOCUMENTS

GB             923449       4/1963

OTHER PUBLICATIONS

Mauro Bassetti et al., "Chemioselectivity in the Presence of Surfactants. I. c-vs. O-Alkylation in β-Dicarbonyl Compounds", Gazette Chimica Italiana, vol. 116, 1986, pp. 583-585.
Okahara, M., Database WPI, Week 199238, Derwent Publication Ltd., London, GB; Class D25, AN 1992-312377 & JP 4217972 A, Aug. 7, 1992 (Abstract).
Agency of Ind Sci & Technology, Database WPI, Week 198929, Derwent Publication Ltd., London, GB; Class B05, AN 1989-211484 & JP 1149751 A, Jun. 12, 1989 (Abstract).
Nippon Mining Co, Database WPI, Week 199315, Derwent Publication Ltd., London, GB; Class A41, AN 1993-121317 & JP 5058955 A, Mar. 9, 1993 (Abstract).
STN International, File CAPLUS, CAPLUS Accession No. 1987:120231, Document No. 106:120231, Texaco Development Corp. "*N-Acylamino Acids*", & JP, A2, 61236760, 19861022.
Erik M. P. Widmark, "*The Kinetics of the Ketonic Decomposition of Aceto-Acetic Acid*", (From the Chemical Laboratory of the Royal Veterinary and Agricultural College, Copenhagen), pp. 393-421. 1920.
Stjerndahl et al., "*Novel Surfactants Preparation, Applications, and Biodegradability*", Surfactant Science Series, vol. 114, 2003, pp. 317-345.
Stjerndahl et al., "*Synthesis and Properties of 2-Alkoxy-N, N-Dimethylethylamine N-Oxides*", Journal of the American Oil Chemists' Society, Surfactants & Detergents, vol. 62, No. 3, Mar. 1985, pp. 555 to 557.

* cited by examiner

*Primary Examiner*—Paul A. Zucker
(74) *Attorney, Agent, or Firm*—Buchanan Ingersoll & Rooney PC

(57) ABSTRACT

Use of a compound having a hydrophobic moiety attached to a hydrophilic moiety, wherein the hydrophilic moiety comprises a β-keto acid group and the hydrophobic moiety is attached via a bond from a carbon or an oxygen of the hydrophobic moiety to a carbon of the β-keto acid group, provided that the β-carbon of the β-keto acid group does not form part of a carboxyl or ester group, or a salt thereof, as a surfactant. A dispersion comprising said surfactant as a dispersing agent. A method for breaking a dispersion comprising said surfactant as a dispersing agent, said method comprising the steps of a) providing said dispersion at a temperature where it is substantially stable; and b) setting the temperature of said dispersion, so as to achieve a desired decomposition rate of the surfactant.

39 Claims, No Drawings

DECOMPOSING SURFACTANT

TECHNICAL FIELD OF THE INVENTION

The present invention relates to the use of a compound having a hydrophobic moiety attached to a hydrophilic moiety, the hydrophilic moiety comprising a β-keto acid group, or a salt thereof, as a surfactant, to a dispersion comprising said surfactant, and to a method for breaking a dispersion.

BACKGROUND ART

So-called cleavable surfactants have been known for several years and the different classes of such surfactants have been nicely reviewed by Stjerndahl et al. in Cleavable Surfactants, Novel Surfactants—Preparation, Applications, and Biodegradability, 2 ed., Holmberg ed., Marcel Dekker, Inc., USA, 2003. A main reason for the development of cleavable surfactants has been environmental concern and a desire for biodegradable surfactants. The main types of cleavable surfactants known today are:
1) Surfactants labile at acidic conditions
2) Surfactants labile at alkaline conditions
3) Light sensitive surfactants
4) Surfactants that degrade in contact with specific chemicals
5) Thermolabile surfactants According to Stjerndahl, most cleavable surfactants contain a hydrolysable bond and thus belong to type 1 or 2. For these surfactants, a change of pH is needed to initiate cleaving of the surfactant. The degradation product is often a soap or a long-chain alcohol, of which at least the former is clearly surface active. Thus, the cleaving of these compounds does not automatically imply that surface activity is lost.

In the case of light sensitive surfactants (type 3), the surfactant has to be exposed to light for a certain amount of time to obtain the desired cleaving.

Surfactants that decompose in contact with specific chemicals (type 4), e.g. ozone cleavable surfactants, are used in specific applications only.

For the group of known thermolabile surfactants (type 5), the decomposition rate is intended to be controlled by regulation of the temperature.

Hayashi et al. (JAOCS, Vol. 62, no. 3 (March 1985), 555–557) report preparation of amine oxide surfactants by oxidation of 2-alkoxy-N,N-dimethylethylamines with hydrogen peroxide. The 2-alkoxy-N,N-dimethylethylamine N-oxide surfactants formed were good foam stabilizers and stable up to 100° C., but decomposed rapidly to vinyl ethers at 150° C. Hence, the decomposition temperature of these surfactants is not compatible with use in aqueous compositions.

GB 923,449 discloses that unsaturated polymerisable compounds can be advantageously polymerised in aqueous medium and in the presence of dispersing agents and activators by using as a dispersing agent a salt of a partial ester of an aliphatic polycarboxylic acid with one or more alcohols having 3 to 20 carbon atoms and heating the resultant polymer emulsion at temperatures between 60 and 200° C. However, these dispersing agents have the drawback of being intrinsically sensitive to alkaline and acidic conditions, causing premature degradation of the surfactant under such conditions.

Conclusively, existing cleavable surfactants and dispersing agents of types 1–4 are either adapted for speciality applications only (being light sensitive or dependent on a specific substance) or cannot be utilised and cleaved at substantially constant pH conditions. Furthermore, cleaving does not always result in loss of surface activity. Existing thermolabile surfactants (type 5) are not suitable in water based applications and/or under alkaline or acidic conditions.

SUMMARY OF THE INVENTION

An object of the present invention is to provide a deactivable thermolabile surfactant, the decomposition rate of which can be controlled within wide limits by altering the temperature in a range starting already at or below room temperature and with no need to go to extremely high temperatures (e.g. over the boiling point of water) for fast decomposition.

Another object of the invention is to provide such a surfactant that is unsusceptible to premature and/or thermally uncontrollable decomposition in a wide pH range (e.g. at alkaline conditions).

Yet another object of the invention is to provide such a surfactant which may be designed to give only non-toxic products upon decomposition.

A further object of the invention is to provide a dispersion comprising such a thermolabile surfactant, said dispersion having a thermally controllable delay time before breaking and a thermally controllable breaking rate.

A further object of the invention is to provide a method for breaking a dispersion.

The above-mentioned objects as well as other objects of the invention, which should be apparent to a person skilled in the art after having studied the description below, are accomplished by the use of a compound having a hydrophobic moiety attached to a hydrophilic moiety, wherein the hydrophilic moiety comprises a β-keto acid group and the hydrophobic moiety is attached via a bond from a carbon or an oxygen of the hydrophobic moiety to a carbon of the β-keto acid group, provided that the β-carbon of the β-keto acid group does not form part of a carboxyl or ester group, or a salt thereof, as a surfactant.

The surfactant of the present invention, has been found to be susceptible to temperature controlled decomposition into $CO_2$, $HCO_3^-$ or $CO_3^{2-}$ (depending on pH) and an oil-like (if liquid), hydrophobic residue, thereby reducing its surface activity. Furthermore, said surfactant is stable to premature and/or thermally uncontrollable degradation over a wide pH range and is thus protected from unintentional decomposition at alkaline, neutral or acidic conditions (generally at $pH \geq pK_a$). Depending on present pH conditions, a salt of the described surfactant may be active.

A further characteristic of the surfactant of the present invention is that its rate of decomposition, and thus its rate of inactivation, can be effectively controlled by temperature at substantially constant pH conditions. Its rate of decomposition is generally increasing with increasing temperature. The rate of decomposition is substantially independent of pH as long as $pH > pK_a$. Furthermore, the decomposition rate of the surfactant of the present invention may be accelerated by catalysts, such as decarboxylases, or simple amino acids, like glycine.

Neither the attachment of the hydrophobic moiety to the hydrophilic moiety via a bond from a carbon of the hydrophobic moiety, nor from an oxygen of the hydrophobic moiety, are susceptible to premature degradation and/or thermally uncontrolled degradation under the above-presented conditions.

In many common situations, e.g. for many commonly used hydrophobic moieties, the hydrophobic moiety is preferably attached via a bond from a carbon of the hydrophobic moiety.

From a synthesis point of view, the hydrophobic moiety is preferably attached to the α-carbon of the β-keto acid group. With respect to the function of the surfactant, however, it may as well be attached to the β-carbon of the β-keto acid group. Optionally, more than one hydrophobic moiety may be attached to the carbon(s) of the hydrophilic moiety. If the hydrophobic moiety is attached to the α-carbon, the β-keto acid group is preferably an acetoacetic acid group. Such a group allows for simple and cost effective synthesis and good function of the surfactant.

It is well known to the skilled man that a wide selection of hydrophobic groups exists and that their detailed structures not always are of critical importance. Thus, any hydrophobic group, not itself susceptible to degradation in aqueous solution, creating an amphiphilic compound when attached to the hydrophilic moiety may be utilised in the present invention. As an example, the hydrophobic moiety may be a straight-chain, branched-chain or cyclic, saturated or unsaturated, optionally substituted, aliphatic group; an optionally substituted aromatic group; an optionally substituted polyoxypropylene group; an optionally substituted perfluoroalkyl group; an optionally substituted polysiloxane group; a lignin or rosin derivative; or a combination thereof.

As used herein, the term "substituted", in relation to the hydrophobic moiety, relates to the substitution of a organic group with any substituents not changing the hydrophobic nature of said moiety or the amphiphilic nature of the compound of the invention.

The hydrophobic moiety is preferably a straight-chain, branched-chain or cyclic, saturated or unsaturated, optionally substituted, aliphatic group; an optionally substituted aromatic group; or a combination thereof. More preferably, the hydrophobic moiety is a straight-chain or branched-chain, saturated or unsaturated, optionally substituted, $C_1$–$C_{30}$ alkyl, or $C_8$–$C_{22}$ alkyl. In a most preferred embodiment, the hydrophobic moiety is dodecyl. Said groups are common, cheap, safe and well-functioning hydrophobic groups.

The compound of the present invention acts as a anionic surfactant (i.e. in its salt form) at $pH \geq pK_a$. The $pK_a$ of compounds of the present invention may vary widely, e.g. as a result of the choice of hydrophobic moieties. Additionally, substitution of the α-carbon of the β-keto acid group with e.g. electron-withdrawing groups, such as $-NO_2$, $CCl_3$, $-CN$, $-COOH$ or $CH_3CO-$, may lower the $pK_a$.

The skilled man is able to chose suitable temperatures (e.g. in the range from 0 to 100° C.) for employing the compound of the present invention.

The surfactant of the present invention may be a dispersing agent.

The objects of the present invention are also accomplished by a dispersion comprising solid particles, liquid droplets or gas bubbles dispersed, as an internal phase, in a fluid, as an external phase, by means of a surfactant, as a dispersing agent, wherein said surfactant is a compound as defined above.

Said surfactant may be active in any kind of dispersion, the preparation of which can be accomplished according to procedures well known to the skilled man (such as agitation, shearing or spraying). As is also well known to the skilled man, a dispersion may be an aerosol, a colloid, an emulsion, a foam, a gel, a sol or a suspension. The external phase of such a dispersion may be an aqueous phase as well as an oil phase. The skilled man is able to routinely examine the decomposition rate, as manifested by delayed dispersion breaking and/or the breaking rate, at different temperatures in such a dispersion (cf. Example 3 below). Accordingly, the skilled man is able to chose suitable temperatures (e.g. in the range from 0 to 100° C.) for employing the dispersion. The rate of decomposition can be effectively controlled by temperature at substantially constant pH conditions. Its rate of decomposition is generally increasing with increasing temperature. The rate of decomposition is substantially independent of pH as long as $pH > pK_a$.

Further, the objects of the present invention are accomplished by a method for breaking a dispersion comprising solid particles, liquid droplets or gas bubbles dispersed, as an internal phase, in a fluid, as an external phase, by means of a surfactant as a dispersing agent, wherein said surfactant is a compound as defined above, said method comprising the steps of a) providing said dispersion at a temperature where it is substantially stable; and b) setting the temperature of said dispersion, so as to achieve a desired decomposition rate of the surfactant.

As described above, the surfactant of the invention is susceptible to an increased rate of decomposition and inactivation by increasing temperature. This property allows for controlled breaking of a dispersion at a desirable moment and/or at a desirable rate. Hence, in any suitable application, the properties of an initially dispersed composition may be changed as desirable.

The skilled man is able to routinely examine the required temperature for a desired decomposition rate. The temperature is dependent on the surfactant, the external phase and the internal phase components, as well as on pH (se above).

The dispersion is preferably provided at a temperature in the range from about 0 to about 40° C., preferably from about 10 to about 30° C., at which the dispersion is virtually stable (i.e. stable for e.g. hours or days).

By raising the temperature to a range from about 40 to about 100° C., preferably from about 60 to about 95° C., the dispersion is broken faster due to increased rate of decomposition and deactivation of the surfactant (i.e. decomposition within e.g. minutes or hours). The rate of decomposition, as manifested by delayed dispersion breaking and/or the breaking rate, can thus be effectively controlled by temperature at substantially constant pH conditions. The rate of decomposition is generally increasing with increasing temperature and is substantially independent of pH as long as $pH > pK_a$.

The dispersion may be provided by i) providing a surfactant precursor, wherein the surfactant precursor is an ester of a compound as defined above;

ii) activating said surfactant precursor to a surfactant, wherein the surfactant is a compound as defined above; and iii) dispersing a mixture of said internal phase, said external phase and said surfactant.

Such provision allows for the surfactant to be stored as its thermostable precursor and be activated shortly before use.

The dispersion may also be provided by i) providing a mixture of said internal phase, said external phase and a surfactant precursor, wherein the surfactant precursor is an ester of a compound as defined above;

ii) activating said surfactant precursor to a surfactant, wherein the surfactant is a compound as defined above; and iii) dispersing said mixture.

Such provision allows for the surface action in a composition comprising the surfactant precursor to be switched on at a desirable occasion, thereby changing the properties of the composition.

A typical characteristic of the surfactant precursor is that it does not degrade or decompose rapidly, even if temperature is raised. Thus, the surfactant of the present invention can be stored in the form of a thermally stabile surfactant precursor, which can quickly be activated to the surfactant of the present invention on-site or just before use. The precursor may be activated (i.e. transformed to the surfactant of the present invention) by saponification or hydrolysis, optionally followed by an adjustment of pH. The concepts of saponification and hydrolysis are well known to the skilled man.

As used herein, the term "β-keto acid group" means a carboxylic acid group having a carbonyl group one carbon removed from the carboxylic acid group, i.e. a group according to formula I.

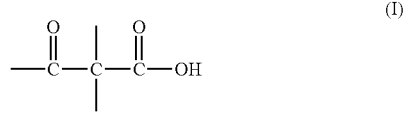

(I)

The "α-carbon" of a β-keto acid group is the carbon next to the carboxylic acid group. The "β-carbon" of a β-keto acid group is the carbon one carbon removed from the carboxylic acid group. See formula II.

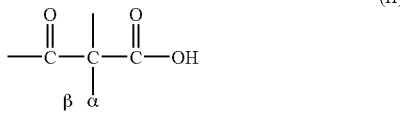

(II)

As used herein, the term "carboxyl group" means a group according to formula III.

(III)

If the β-carbon of the β-keto acid group forms part of such a carboxyl group, the compound of the present invention will not lose its surface activity upon decomposition.

As used herein, the term "ester group" means a group according to formula IV.

(IV)

If the β-carbon of the β-keto acid group forms part of such an ester group, the compound of the present invention may, before or after decomposition, be hydrolysed into a further surface active compound.

EXAMPLES

Example 1

Synthesis of a Surfactant Precursor

Sodium metal (1.8 g, 0.075 mol) was added in small portions to a two-necked vessel containing abs. ethanol (30 mL) with continuous stirring under $N_2$ until all Na was dissolved. Then ethyl acetoacetate (14.7 mL, 0.115 mol) and 1-iodododecane (18.7 mL, 0.076 mol) were added to the vessel and the resultant mixture was refluxed for 3.5 h and then poured onto water and extracted with diethyl ether. The obtained extract was dried over $MgSO_4$ and concentrated in vacuum. The residue was purified with vacuum distillation (0.1 bar, fraction collected at 135–140° C.) giving a clear oil.

The obtained oil was characterised by nuclear magnetic resonance ($^1H$ NMR) and found to consist of approximately 98.5% pure ethyl α-dodecylacetoacetate. $^1H$ NMR peaks were obtained at the following shifts (ppm): 0.90, 1.35, (1.65 and 1.67), 1.85, (2.05), 2.25, 3.42, 4.22. In addition, the typical peaks from chloroform and dichloromethane were obtained, originating from the solvent used. Peaks within parenthesis were small unidentified peaks from impurities.

Example 2a

Activation of the Surfactant Precursor through Saponifiaction 100 mg of the surfactant precursor from Example 1 was mixed with 700 μL of 0.5 M KOH dissolved in ethanol and the mixture was left standing with continuous stirring for one hour. The mixture was then poured into 10 mL of deionised water. The resulting product was shown to exhibit a behaviour typical for concentrated solutions of water-soluble surfactants of the soap-type, i.e. it gave heavily foaming turbid aqueous solutions and allowed the formation of very stabile oil-in-water emulsions. The fact that the formed emulsions were indeed oil-in-water emulsions (and not water-in-oil emulsions) was proven according to Example 2c.

Example 2b

Activation of the Surfactant Precursor through Saponifiaction

Precursor activation was performed according to Example 2a. However, to obtain a more pure active surfactant the precursor was extracted several times with deionised water prior to saponification. Additionally, the saponification time was increased to three hours.

Example 2c

Test of Type of Emulsion Obtained

Equal amounts of hexadecane (oil, coloured red for visibility by a small amount of oil soluble pigment) and water containing 0.85% of the surfactant (activated precursor) from Example 2a was exposed to vigorous shearing by a so-called Ultraturrax mixer equipment. Upon dropping of a drop of the obtained emulsion into pure hexadecane, the droplet was seen to fall to the bottom of the beaker unaffected. Another droplet of the obtained emulsion was dropped into water, and the emulsion droplet was then seen to spontaneously disperse in the water, which proves that the emulsion was of the oil-in water type (the continuous medium of the emulsion being water, not oil).

Example 2d

Test of Hydrophilic/Hydrophobic Character of the Precursor

The precursor ester from Example 1 was added as one drop to a sample of deionised water. The precursor exhibited an oil-like (hydrophobic) behaviour as expected from its chemical structure.

Example 3

Formation of Oil-in-Water Emulsions with Delayed Breaking and Temperature-Controlled Rate of Breaking Samples taken from an emulsion prepared as described in Example 2c, withdrawn from the emulsion during continuous stirring by a magnetic stirrer, were subjected to isothermal heat-treatment at temperatures from room temperature up to 95° C. and documented photographically as a function of time. The percentage of oil separated at a given time was measured from obtained photos and is shown in Table 1.

TABLE 1

| | Separated oil (%) | | | | | |
|---|---|---|---|---|---|---|
| Time (min) | Room temperature | 40° C. | 50° C. | 60° C. | 70° C. | 95° C. |
| 5 | 0.0 | 0.0 | 0.0 | 0.0 | 0.0 | 0.0 |
| 10 | 0.0 | 0.0 | 0.0 | 0.0 | 0.0 | 0.0 |
| 20 | 0.0 | 0.0 | 0.0 | 0.0 | 0.0 | 2.9 |
| 25 | 0.0 | 0.0 | 0.0 | 0.0 | 0.0 | 6.7 |
| 30 | 0.0 | 0.0 | 0.0 | 0.0 | 0.0 | 8.6 |
| 40 | 0.0 | 0.0 | 0.0 | 0.0 | 0.0 | 11.4 |
| 50 | 0.0 | 0.0 | 0.0 | 0.0 | 0.0 | 11.7 |
| 65 | 0.0 | 0.0 | 0.0 | 0.0 | 0.0 | 19.2 |
| 80 | 0.0 | 0.0 | 0.0 | 0.0 | 6.7 | 24.0 |
| 95 | 0.0 | 0.0 | 0.0 | 2.9 | 13.3 | 29.7 |
| 115 | 0.0 | 0.0 | 0.0 | 3.8 | 19.0 | 31.7 |
| 135 | 0.0 | 0.0 | 0.0 | 3.8 | 26.7 | 36.5 |
| 180 | 0.0 | 0.0 | 0.0 | 5.7 | 40.0 | 47.3 |
| 215 | 0.0 | 0.0 | 0.0 | 11.4 | 43.8 | 49.0 |
| 250 | 0.0 | 0.0 | 0.0 | 20.0 | 51.4 | 58.8 |
| 310 | 0.0 | 0.0 | 2.0 | 28.6 | 58.1 | 59.2 |
| 370 | 0.0 | 0.0 | 10.0 | 40.0 | 66.7 | 69.3 |
| 430 | 0.0 | 0.0 | 19.2 | 46.7 | 65.7 | 75.1 |
| 440 | 0.0 | 0.0 | 50.0 | 62.4 | 67.3 | 80.4 |
| 475 | 0.0 | 3.0 | 54.7 | 68.6 | 76.5 | 82.2 |
| 510 | 0.0 | 4.0 | 56.0 | 68.3 | 77.7 | 83.3 |
| 545 | 0.0 | 5.1 | 55.0 | 69.3 | 82.9 | 84.2 |
| 630 | 0.0 | 7.1 | 60.0 | 78.8 | 87.0 | 89.1 |
| 710 | 0.0 | 5.1 | 60.0 | 79.6 | 86.5 | 88.2 |
| 840 | 0.0 | 8.8 | 69.3 | 83.9 | 85.7 | 89.2 |
| 870 | 0.0 | 33.7 | 78.4 | 87.0 | 87.4 | 88.8 |
| 1045 | 0.0 | 31.7 | 79.2 | 86.1 | 85.7 | 92.1 |
| 1175 | 0.0 | 40.0 | 79.6 | 88.2 | 85.7 | 90.5 |

As can be seen in Table 1, a delay-time before initiation of emulsion-breaking was observed. This delay time was found to be clearly controllable by temperature, e.g. the delay-time was short at high temperatures and substantially longer at lower temperatures. In addition the rate of emulsion-breaking (after it had started) was lower at low temperatures than at high temperatures.

Note that the absolute delay-times and emulsion breaking rates will likely depend heavily on the emulsification protocol and history of the individual samples. The general relative trends, with higher rates and shorter delay-times at high temperatures as compared to low temperatures, will however still be valid for a given individual emulsion sample.

Example 4

Verification of Decay of Surface Activity via Monitoring of a Decay in Foaminess Samples containing 0.85% of surfactant, prepared as in Example 2a above, was heat-treated at a series of different temperatures in water baths and the initial foam-height obtained upon direct shaking of the hot samples was recorded as a function of time. As can be seen from Table 2, the foaminess of the samples decayed with time, and did so significantly quicker at higher temperatures. This shows, again, that the surfactants of the present invention allows for control of the rate of, decay of surface activity within a wide range.

TABLE 2

| | Foam height (cm) | | | | | |
|---|---|---|---|---|---|---|
| Time (min) | Room temperature | 40° C. | 50° C. | 60° C. | 70° C. | 95° C. |
| 5 | 6.05 | 5.7 | 5.55 | 5.3 | 5.25 | 4.35 |
| 10 | 5.9 | 5.75 | 5.4 | 5.25 | 5.4 | 1.6 |
| 20 | 5.95 | 6.05 | 5.85 | 5.4 | 5.4 | 1.05 |
| 25 | 6.1 | 6.15 | 5.75 | 5.7 | 5.25 | 0.85 |
| 45 | 5.9 | 5.85 | 6.1 | 5.75 | 4.7 | 0.85 |
| 60 | 5.8 | 6.05 | 6.05 | 5.45 | 4.85 | 0.9 |
| 80 | 5.8 | 5.55 | 5.7 | 4.95 | 4.05 | 0.8 |
| 100 | 5.85 | 5.5 | 5.6 | 5.1 | 2.8 | 0.85 |
| 115 | 6.1 | 5.7 | 5.8 | 5 | 2.7 | 0.8 |
| 135 | 5.95 | 5.85 | 5.5 | 4.6 | 1.7 | 0.85 |
| 180 | 5.7 | 5.85 | 5.8 | 4.75 | 1.55 | 0.75 |
| 215 | 5.65 | 5.85 | 4.65 | 4.5 | 1 | 0.75 |
| 255 | 5.55 | 5.7 | 4.7 | 3.65 | 0.85 | 0.8 |
| 315 | 5.6 | 5.85 | 4.85 | 3.7 | 0.9 | 0.8 |
| 375 | 5.75 | 5.65 | 3.5 | 3.4 | 0.7 | 0.8 |
| 425 | 5.6 | 5.75 | 3.5 | 2.55 | 0.7 | 0.85 |
| 440 | 5.7 | 5.35 | 2.25 | 1.85 | 0.7 | 0.8 |
| 470 | 5.7 | 5.45 | 2.3 | 1.8 | 0.75 | 0.8 |
| 505 | 5.55 | 5.35 | 2.65 | 1.45 | 0.75 | 0.9 |
| 625 | 5.55 | 4.4 | 2.35 | 1.15 | 0.75 | 0.9 |
| 705 | 5.6 | 3.8 | 2.35 | 1.15 | 0.8 | 0.9 |
| 835 | 5.55 | 3.75 | 1.65 | 1.35 | 0.8 | 0.9 |
| 870 | 4.15 | 2.75 | 0.65 | 0.7 | 0.65 | 0.9 |
| 1100 | 4.1 | 2.55 | 0.75 | 0.9 | 0.75 | 0.9 |
| 1230 | 4.25 | 1.85 | 1 | 0.85 | 0.38 | 0.9 |

Example 5

Verification of the Obtained Degradation Product

A sample consisting of 0.85% aqueous solutions of the surfactant (see above-mentioned Examples) was treated for 31 hours at 95° C. and thereafter stored in a refrigerator. The sample was then cooled on an ice bath and centrifuged. A crystalline phase was thereby obtained floating on top of the centrifuged liquid. The crystals were removed from the liquid and washed once with water through vigorous shaking followed by centrifugation and separation. The obtained crystals were dissolved in deuterated acetone and characterised by $^1$H NMR. The results confirmed that pentadecanone had been formed, which verifies the expected decomposition mechanism of the surfactant (the activated/ saponified surfactant precursor). Pentadecanone is non-toxic and allowed in food applications.

Example 6 pH Interval of Foaming

An aqueous solution sample of surfactant (activated precursor according to Example 2b) was pH adjusted with HCl, so as to detect the lower pH limit for foaming (assumed to coincide with the $pK_a$ of the surfactant). It was found that solutions foamed well down to, and including pH 6 but that a sample of pH 5 did not foam. This demonstrates the soap/fatty acid like character of the active decomposable surfactant of this invention and also shows that the typical pH interval of usefulness-in aqueous media can be e.g. from 6 to 14 (see below).

Example 7 pH Dependence of the Delay of Emulsion Breaking

Several emulsions of hexadecane in an aqueous solution containing 0.085% surfactant (activated precursor according to Example 2b) were prepared using an Ultraturrax equipment as above. Thereafter, the pH of the emulsion samples were adjusted to 14, 12, 10, 8 and 6 with 1 M HCl or 1 M NaOH. The samples were then treated at 95 and 70° C. and the percentage of oil separated was followed as a function of time. Table 3 shows the results obtained at 95 and 70° C. As can be seen from the table, delayed emulsion breaking was clearly obtained for all samples with pH higher than or equal to 10. The delay time was not dependent on pH in this interval ($pH \geq pK_a$), which is to be expected from acetoacetate decomposition (Widmark, Acta med. Scand., Vol. 53 (1920–21), 393–421).

For the samples with pH 8 some oil had separated already before the heat-treatment. However, the sample treated at 70° C. still displayed a delayed onset of further breaking when heated. The initial non-emulsified oil in these sample was probably due to poor emulsification, as later tests gave emulsions with stability at room temperature.

As can be seen from the table, both samples at pH 6 clearly began separating without any delay. This is in accordance with the typical kinetics of acetoacetate decomposition (Widmark, Acta med. Scand., Vol. 53 (1920–21), 393–421) as the rate of decomposition is expected to increase as pH comes close to, or below the $pK_a$ of the surfactant.

Example 8 pH Dependence of the Delay of Emulsion Breaking

Emulsified samples (pH 8, 10 and 14) were treated at room temperature and at 7° C. All emulsions apart from the sample with pH 8, which was stored at room temperature, were stable for more than 19 hours. For the sample with pH 8, stored at room temperature, a weak initiation of oil separation in the form of small oil droplets forming at the top of the test tube was detected at a time 19 hours after the emulsion was prepared.

TABLE 3

| Time (min) | Separated oil (%) | | | | | | | | | |
|---|---|---|---|---|---|---|---|---|---|---|
| | pH 6 70° C. | pH 6 95° C. | pH 8 70° C. | pH 8 95° C. | pH 10 70° C. | pH 10 95° C. | pH 12 70° C. | pH 12 95° C. | pH 14 70° C. | pH 14 95° C. |
| 0 | 16 | 12 | 15 | 14 | 0 | 0 | 0 | 0 | 0 | 0 |
| 10 | 29 | 34 | 13 | 20 | 0 | 0 | 0 | 0 | 0 | 0 |
| 20 | 34 | 47 | 13 | 35 | 0 | 0 | 0 | 0 | 0 | 13 |
| 35 | 67 | 67 | 15 | 67 | 0 | 29 | 0 | 19 | 0 | 40 |
| 55 | 79 | 70 | 16 | 82 | 0 | 43 | 0 | 28 | 0 | 43 |
| 75 | 85 | 72 | 54 | 91 | 8 | 57 | 23 | 42 | 27 | 65 |
| 95 | 87 | 81 | 73 | 92 | 28 | 69 | 48 | 56 | 45 | 80 |
| 120 | 87 | 79 | 93 | 95 | 53 | 70 | 69 | 67 | 65 | 92 |
| 150 | 95 | 67 | 93 | 97 | 68 | 76 | 81 | 70 | 67 | 92 |
| 255 | 89 | 85 | 100 | 96 | 92 | 80 | 93 | 81 | 92 | 92 |

The invention claimed is:

1. A dispersion comprising solid particles, liquid droplets or gas bubbles dispersed, as an internal phase, in a fluid, as an external phase, by means of a surfactant, as a dispersing agent, wherein said surfactant is a compound having a hydrophobic moiety attached to a hydrophilic moiety, wherein the hydrophilic moiety comprises a β-keto acid group and the hydrophobic moiety is attached via a bond from a carbon or an oxygen of the hydrophobic moiety to a carbon of the β-keto acid group, provided that the β-carbon of the β-keto acid group does not form part of a carboxyl or ester group, or a salt thereof.

2. A dispersion according to claim 1, wherein the hydrophobic moiety is attached via a bond from a carbon of the hydrophobic moiety to a carbon of the β-keto acid group.

3. A dispersion according to claim 1, wherein the hydrophobic moiety is attached to the α-carbon of the β-keto acid group.

4. A dispersion according to claim 1, wherein the hydrophobic moiety is attached to the β-carbon of the β-keto acid group.

5. A dispersion according to claim 3, wherein the hydrophilic moiety is an acetoacetic acid group.

6. A dispersion according to claim 1, wherein the hydrophobic moiety is a straight-chain, branched-chain or cyclic, saturated or unsaturated, optionally substituted, aliphatic group; an optionally substituted aromatic group; an optionally substituted polyoxypropylene group; an optionally substituted perfluoroalkyl group; an optionally substituted polysiloxane group; a lignin or rosin derivative; or a combination thereof.

7. A dispersion according to claim 6, wherein the hydrophobic moiety is a straight-chain, branched-chain or cyclic, saturated or unsaturated, optionally substituted, aliphatic group; an optionally substituted aromatic group; or a combination thereof.

8. A dispersion according to claim 7, wherein the hydrophobic moiety is a straight-chain or branched-chain, saturated or unsaturated, optionally substituted, $C_1$–$C_{30}$ alkyl.

9. A dispersion according to claim 8, wherein the hydrophobic moiety is a straight-chain or branched-chain, saturated or unsaturated, optionally substituted, $C_8$–$C_{22}$ alkyl.

10. A dispersion according to claim 9, wherein the hydrophobic moiety is dodecyl.

11. A dispersion according to claim 1, wherein the surfactant is an anionic surfactant.

12. A dispersion according to claim 1, which is an aerosol, a colloid, an emulsion, a foam, a gel, a sol or a suspension.

13. A method for breaking a dispersion comprising solid particles, liquid droplets or gas bubbles dispersed, as an internal phase, in a fluid, as an external phase, by means of a surfactant as a dispersing agent, wherein said surfactant is a compound having a hydrophobic moiety attached to a hydrophilic moiety, wherein the hydrophilic moiety comprises a β-keto acid group and the hydrophobic moiety is attached via a bond from a carbon or an oxygen of the hydrophobic moiety to a carbon of the β-keto acid group, provided that the β-carbon of the β-keto acid group does not form part of a carboxyl or ester group, or a salt thereof, said method comprising the steps of
   a) providing said dispersion at a temperature where it is substantially stable; and
   b) setting the temperature of said dispersion, so as to achieve a desired decomposition rate of the surfactant.

14. A method according to claim 13, wherein step a) is performed at a temperature in the range from about 0 to about 40° C.

15. A method according to claim 13, wherein step b) is performed by raising the temperature to a range from about 40 to about 100° C.

16. A method according to claim 13, wherein step a) is performed by
   i) providing a surfactant precursor, wherein the surfactant precursor is an ester of said compound;
   ii) activating said surfactant precursor to said surfactant; and
   iii) dispersing a mixture of said internal phase, said external phase and said surfactant.

17. A method according to claim 13, wherein step a) is performed by
   i) providing a mixture of said internal phase, said external phase and a surfactant precursor, wherein the surfactant precursor is an ester of said compound;
   ii) activating said surfactant precursor to said surfactant; and
   iii) dispersing said mixture.

18. A method according to claim 16, wherein said surfactant precursor is activated by saponification or hydrolysis.

19. A method according to claim 13, wherein step a) is performed at a temperature in the range from about 10 to about 30° C.

20. A method according to claim 13, wherein step b) is performed by raising the temperature to a range from about 60 to about 95° C.

21. A method according to claim 14, wherein step b) is performed by raising the temperature to a range from about 40 to about 100° C.

22. A method according to claim 14, wherein step b) is performed by raising the temperature to a range from about 60 to about 95° C.

23. A method according to claim 14, wherein step a) is performed by
   i) providing a surfactant precursor, wherein the surfactant precursor is an ester of said compound;
   ii) activating said surfactant precursor to said surfactant; and
   iii) dispersing a mixture of said internal phase, said external phase and said surfactant.

24. A method according to claim 15, wherein step a) is performed by
   i) providing a surfactant precursor, wherein the surfactant precursor is an ester of said compound;
   ii) activating said surfactant precursor to said surfactant; and
   iii) dispersing a mixture of said internal phase, said external phase and said surfactant.

25. A method according to claim 14, wherein step a) is performed by
   i) providing a mixture of said internal phase, said external phase and a surfactant precursor, wherein the surfactant precursor is an ester of said compound;
   ii) activating said surfactant precursor to said surfactant; and
   iii) dispersing said mixture.

26. A method according to claim 15, wherein step a) is performed by
   i) providing a mixture of said internal phase, said external phase and a surfactant precursor, wherein the surfactant precursor is an ester of said compound;
   ii) activating said surfactant precursor to said surfactant; and
   iii) dispersing said mixture.

27. A method according to claim 17, wherein said surfactant precursor is activated by saponification or hydrolysis.

28. A method for reducing the surface tension of a liquid or the interfacial tension between a liquid and another phase, comprising adding to said liquid as a surfactant a compound having a hydrophobic moiety attached to a hydrophilic moiety, wherein the hydrophilic moiety comprises a β-keto acid group and the hydrophobic moiety is attached via a bond from a carbon or an oxygen of the hydrophobic moiety to a carbon of the β-keto acid group, provided that the β-carbon of the β-keto acid group does not form part of a carboxyl or ester group, or a salt thereof.

29. A method according to claim 28 wherein the hydrophobic moiety is attached via a bond from a carbon of the hydrophobic moiety to a carbon of the β-keto acid group.

30. A method according to claim 28 wherein the hydrophobic moiety is attached to the α-carbon of the β-keto acid group.

31. A method according to claim 28 wherein the hydrophobic moiety is attached to the β-carbon of the β-keto acid group.

32. A method according to claim 30 wherein the hydrophilic moiety is an acetoacetic acid group.

33. A method according to claim 28 wherein the hydrophobic moiety is a straight-chain, branched-chain or cyclic, saturated or unsaturated, optionally substituted, aliphatic group; an optionally substituted aromatic group; an optionally substituted polyoxypropylene group; an optionally substituted perfluoroalkyl group; an optionally substituted polysiloxane group; a lignin or rosin derivative; or a combination thereof.

34. A method according to claim 33 wherein the hydrophobic moiety is a straight-chain, branched-chain or cyclic, saturated or unsaturated, optionally substituted, aliphatic group, an optionally substituted aromatic group; or a combination thereof.

35. A method according to claim 34 wherein the hydrophobic moiety is a straight-chain or branched-chain, saturated or unsaturated, optionally substituted, $C_1$–$C_{28}$ alkyl.

36. A method according to claim 35 wherein the hydrophobic moiety is a straight-chain or branched-chain, saturated or unsaturated, optionally substituted $C_8$–$C_{22}$ alkyl.

37. A method according to claim 36 wherein the hydrophobic moiety is dodecyl.

38. A method according to claim 28 wherein the surfactant is an anionic surfactant.

39. A method according to claim 28 wherein said surfactant is a dispersing agent.

* * * * *